US010610667B2

(12) United States Patent
Munsinger et al.

(10) Patent No.: US 10,610,667 B2
(45) Date of Patent: Apr. 7, 2020

(54) MICRO SUPPORT CATHETER

(71) Applicant: BOSTON SCIENTIFIC SCIMED, INC., Maple Grove, MN (US)

(72) Inventors: Joel Munsinger, Blaine, MN (US); Joel WasDyke, Eden Prairie, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 368 days.

(21) Appl. No.: 15/152,119

(22) Filed: May 11, 2016

(65) Prior Publication Data
US 2016/0331325 A1    Nov. 17, 2016

Related U.S. Application Data

(60) Provisional application No. 62/161,146, filed on May 13, 2015.

(51) Int. Cl.
*A61M 25/00* (2006.01)
*A61M 25/09* (2006.01)

(52) U.S. Cl.
CPC ........ *A61M 25/0068* (2013.01); *A61M 25/09* (2013.01); *A61M 25/005* (2013.01)

(58) Field of Classification Search
CPC ........................... A61M 25/0068; A61M 25/09
USPC ....................................................... 600/585
See application file for complete search history.

(56) References Cited

U.S. PATENT DOCUMENTS

| | | | |
|---|---|---|---|
| 5,131,407 A * | 7/1992 | Ischinger | A61M 25/09041 600/434 |
| 5,238,004 A | 8/1993 | Sahatjian et al. | |
| 5,514,128 A | 5/1996 | Hillsman et al. | |
| 5,643,251 A | 7/1997 | Hillsman et al. | |
| 6,102,890 A * | 8/2000 | Stivland | A61M 25/0054 604/96.01 |
| 6,406,442 B1 * | 6/2002 | McFann | A61B 17/221 600/434 |
| 6,508,803 B1 | 1/2003 | Horikawa et al. | |
| 7,744,545 B2 | 6/2010 | Aimi et al. | |
| 8,043,232 B2 | 10/2011 | Osborne | |
| 8,109,888 B2 | 2/2012 | Terashi et al. | |
| 8,262,588 B2 | 9/2012 | Miyata et al. | |
| 2005/0119615 A1 | 6/2005 | Noriega et al. | |
| 2006/0074442 A1 | 4/2006 | Noriega et al. | |
| 2008/0140101 A1 | 6/2008 | Carley et al. | |
| 2013/0046285 A1 * | 2/2013 | Griffin | A61M 25/0013 604/527 |
| 2014/0058324 A1 * | 2/2014 | Salahieh | A61B 1/00135 604/95.04 |

(Continued)

*Primary Examiner* — Daniel L Cerioni
(74) *Attorney, Agent, or Firm* — Seager, Tufte & Wickhem, LLP

(57) ABSTRACT

A catheter system comprising a guidewire and a support catheter is disclosed. The support catheter may comprise an elongate shaft having a proximal region, a distal region, and a lumen extending therebetween. The support catheter may further comprise a helical section extending distally from the distal region of the elongate shaft. The helical section may comprise a tubular member wound into a plurality of rings a lumen in communication with the lumen of the elongate shaft. The plurality of rings may each have an outer diameter. A minimum diameter of each of the outer diameters may be greater than an outer diameter of the elongate shaft.

13 Claims, 12 Drawing Sheets

(56) References Cited

U.S. PATENT DOCUMENTS

2015/0359589 A1\* 12/2015 Mauch ................. A61M 25/09
                                                            606/41

\* cited by examiner

MICRO SUPPORT CATHETER

CROSS-REFERENCE TO RELATED APPLICATIONS

This application claims priority under 35 U.S.C. § 119 to U.S. Provisional Application Ser. No. 62/161,146, filed May 13, 2015, the entirety of which is incorporated herein by reference.

TECHNICAL FIELD

The present disclosure pertains to medical devices, and methods for manufacturing medical devices. More particularly, the present disclosure pertains to elongated intracorporeal medical devices including a tubular member connected with other structures, and methods for manufacturing and using such devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example medical device comprises:

an elongate shaft having a proximal region, a distal region, and a lumen extending therebetween;

a helical section extending distally from the distal region of the elongate shaft, the helical section comprising a tubular member wound into a helix; and a manifold affixed to the proximal region of the elongate shaft;

wherein the plurality of rings each have an outer diameter and the smallest of any of the outer diameters of the plurality of rings is greater than an outer diameter of the elongate shaft.

Alternatively or additionally to any of the embodiments above, the helix may comprise a ring having less than a 360° revolution.

Alternatively or additionally to any of the embodiments above, the helix may comprise a plurality of rings including a proximal ring, a distal ring, and one or more intermediate rings disposed between the proximal ring and the distal ring.

Alternatively or additionally to any of the embodiments above, the outer diameter of each of plurality of rings is variable.

Alternatively or additionally to any of the embodiments above, the proximal ring and the distal ring each have an outer diameter less than an outer diameter of the one or more intermediate rings.

Alternatively or additionally to any of the embodiments above, the outer diameter of each of plurality of rings is the same.

Alternatively or additionally to any of the embodiments above, a pitch of the helical section varies from a proximal end of the helical section to a distal end of the helical section.

Alternatively or additionally to any of the embodiments above, a pitch of the helical section is the same from a proximal end of the helical section to a distal end of the helical section.

Alternatively or additionally to any of the embodiments above, further comprising a plurality of slots in a wall of the tubular member.

Alternatively or additionally to any of the embodiments above, further comprising a braided element extending along a portion of the tubular member.

Alternatively or additionally to any of the embodiments above, further comprising a coiled element extending along a portion of the tubular member.

Alternatively or additionally to any of the embodiments above, the tubular member comprises a polymeric material.

An example catheter system comprises:

a guidewire including a proximal end region and a distal end region;

an elongate shaft having a proximal region, a distal region, and a lumen extending therebetween, the lumen configured to slidably receive the guidewire;

a helical section extending distally from the distal region of the elongate shaft, the helical section comprising a tubular member wound into a plurality of rings and having a lumen in communication with the lumen of the elongate shaft; and a manifold affixed to the proximal region of the elongate shaft;

wherein the plurality of rings each have an outer diameter and the smallest of any of the outer diameters of the plurality of rings is greater than an outer diameter of the elongate shaft.

Alternatively or additionally to any of the embodiments above, the proximal end region of the guidewire has a first flexibility and the distal end region of the guidewire has a second flexibility greater than the first flexibility.

Alternatively or additionally to any of the embodiments above, the tubular member has a third flexibility more than the first flexibility of the guidewire and less than the second flexibility of the guidewire.

Alternatively or additionally to any of the embodiments above, when the tubular member is disposed over the proximal end region of the guidewire, the guidewire biases the tubular member into a straight configuration.

Alternatively or additionally to any of the embodiments above, when the tubular member is disposed over the distal end region of the guidewire, the tubular member biases the guidewire into a helical configuration.

Alternatively or additionally to any of the embodiments above, wherein the plurality of rings comprises a proximal ring, a distal ring, and one or more intermediate rings disposed between the proximal ring and the distal ring.

An example method of placing a guidewire comprises:

advancing a guidewire through a patient's vasculature to a first location, the guidewire comprising a proximal end region and a distal end region;

advancing a support catheter over the guidewire, the support catheter comprising:

an elongate shaft having a proximal region, a distal region, and a lumen extending therebetween, the lumen configured to slidably receive the guidewire; and a helical section extending distally from the distal region of the elongate shaft, the helical section comprising a tubular member wound into a plurality of rings and having a lumen in communication with the lumen of the elongate shaft;

advancing the support catheter beyond a distal end of the guidewire;

locating a distal end of the support catheter in a second location in the patient's vasculature;

advancing the guidewire distally beyond the distal end of the support catheter after locating the distal end of the support catheter at the second location; and removing the support catheter.

Alternatively or additionally to any of the embodiments above, the proximal end region of the guidewire has a first flexibility and the distal end region of the guidewire has a second flexibility greater than the first flexibility.

Alternatively or additionally to any of the embodiments above, the tubular member has a third flexibility more than the first flexibility of the guidewire and less than the second flexibility of the guidewire.

Alternatively or additionally to any of the embodiments above, when the tubular member is disposed over the proximal end region of the guidewire, the guidewire biases the tubular member into a straight configuration.

Alternatively or additionally to any of the embodiments above, when the tubular member is disposed over the distal end region of the guidewire, the tubular member biases the guidewire into a helical configuration.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
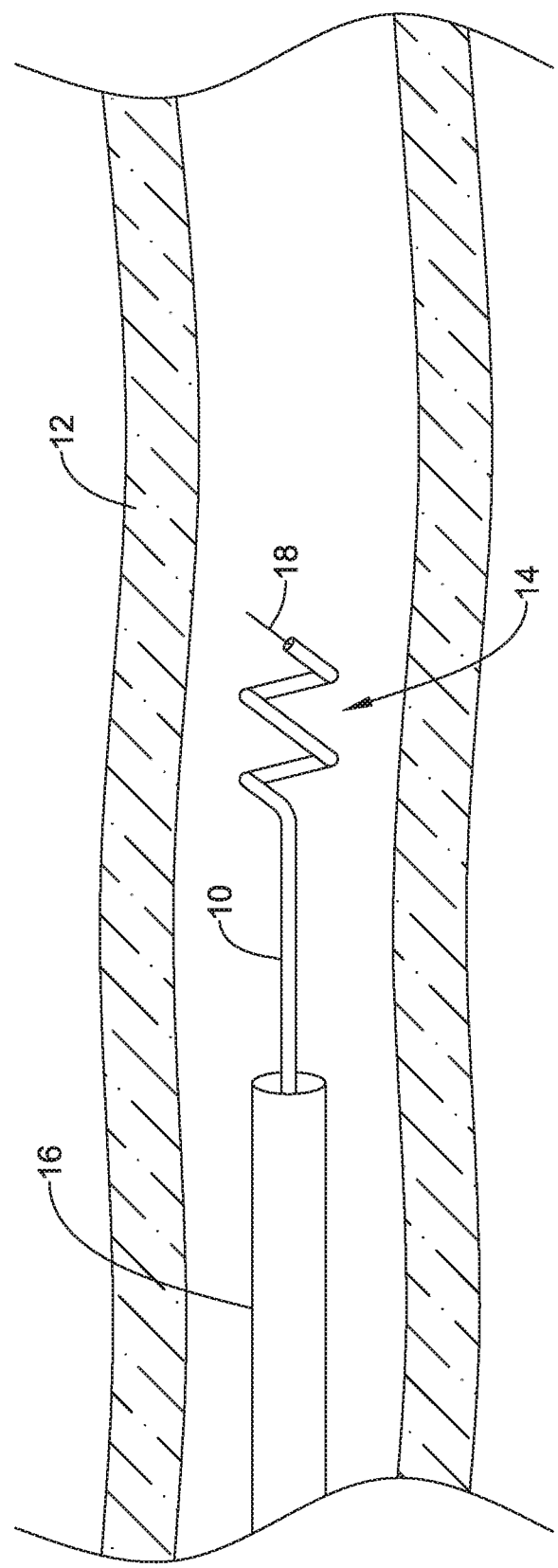
FIG. 1 is a plan view of an embodiment of a medical device according to the invention disposed in a blood vessel.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

FIG. 1 is a plan view of an embodiment of a medical device 10, for example a support catheter, disposed in a blood vessel 12. Although the medical device 10 is depicted in FIG. 1 as a support catheter, it is not intended to be limited to just being a support catheter. Indeed, medical device 10 may take the form of other suitable guiding, diagnosing, or treating device (including catheters, endoscopic instruments, laparoscopic instruments, etc., and the like) and it may be suitable for use at other locations and/or body lumens within a patient. The support catheter 10 may include a distal section 14 that may be generally configured for probing within the anatomy of a patient. The support catheter 10 may be used for intravascular procedures. For example, the support catheter 10 may be used in conjunction with another medical device 16, which may take the form of a catheter, to treat and/or diagnose a medical condition and/or a guidewire 18. Of course, numerous other uses are known amongst clinicians for guidewires, catheters, and other similarly configured medical devices.

In some instances, the support catheter 10 may be used to facilitate placement of a guidewire, such as guidewire 18 into small side branches or accessory vessels. It may be desirable to minimize catheter axial bias as the catheter 10 is torqued in order to gain access to a side branch or accessory vessel. The distal section 14 of the support catheter 10 may have a helical shape that may allow a user non-axial bias torqueing of the support member as they target side branch and accessory vessel guidewire access, as will be discussed in more detail below.

Figure 2:
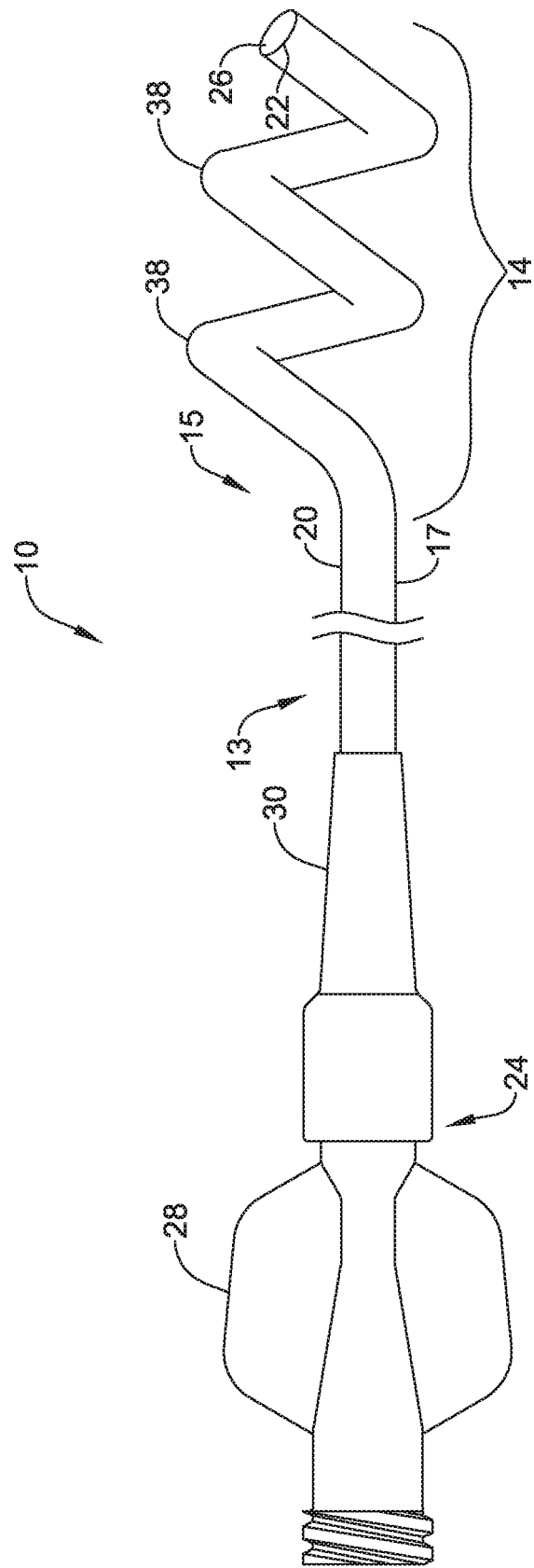
FIG. 2 is an embodiment of a medical device according to the invention.

FIG. 2 is a side view of an illustrative support catheter 10. The support catheter 10 may include a generally elongate shaft 20 having a proximal portion 13, a distal portion 15 terminating at a distal end 22, and an intermediate region 17 disposed between the proximal portion 13 and the distal portion 15. The elongate shaft 20 may extend proximally from the distal end 22 to the proximal portion 13 which may be configured to remain outside of a patient's body. The proximal portion 13 of the elongate shaft 20 may include a manifold 24 attached thereto for connecting other treatment devices or providing a port for facilitating other treatments. The manifold 24 may include a hub 28 and strain relief 30. It is contemplated that the stiffness and size of the elongate shaft 20 may be modified to form a support catheter 10 for use in various locations within the body. In some embodiments, the elongate shaft 20 may have an inner diameter in the range of 0.017-0.021 inches (0.43-0.53 millimeters). The elongate shaft 20 may further define a lumen 26 through which a guidewire 18 (shown in FIG. 1) may be passed in order to advance the catheter to a predetermined position, although this is not required. The support catheter 10 may be configured to be advanced through a working channel of a catheter, guide sheath, delivery sheath, or other medical device 16 (shown in FIG. 1).

The distal section 14 of the support catheter 10 may generally take the form of a helix including a plurality of windings or rings 38. The size and spacing of the rings 38 may be varied, as will be discussed in more detail below. The helical shape of the distal section 14 may allow the user non-axial bias torqueing of the support member as they target side branch and accessory vessel guidewire access. The distal section 14 may be formed from a polymeric material having a stiffness that is greater than a stiffness of a distal end region of a guidewire. For example, a guidewire can be tracked into position and the support catheter 10 may then be tracked over the guidewire. As the distal section 14 of the support catheter 10 is tracked over the proximal, stiffer portion of the guidewire, the distal section 14 of the support catheter 10 is straightened to allow for easier advancement of the support catheter 10. As the distal section 14 is tracked over the more flexible distal end region of the guidewire, the distal section 14 overcomes the bias of the guidewire and resumes its generally helical shape. The distal section 14 can then be used to access the target side branch or accessory vessel. The helical shape of the distal section 14 may help keep the elongate shaft 20 centered in the vessel while also preventing the distal end 22 from dragging on the vessel wall. Once vessel access is gained the guidewire can be advanced. As stiffer wire segments pass through the support catheter 10, the distal section 14 may again straighten out and allow typical guidewire advancement. Once vessel access is ensured the support catheter 10 may be removed and/or exchanged for more traditional interventional products.

In some embodiments, the distal section 14 may comprise a polymeric tubular element attached (e.g. weld, melt, bond, etc.) to the distal portion 15 of the elongate shaft 20. Alternatively, the distal section 14 may be formed as a unitary structure with the elongate shaft 20. The polymeric material may be selected such that the distal section 14 is substantially flexible to straighten while being advanced over a proximal region of the guidewire, yet rigid enough to overcome the bias of a distal region of the guidewire. It is contemplated that the distal section 14 may have a stiffness less than a proximal region of a guidewire but greater than a distal region of the guidewire. In other embodiments, the distal section 14 may be formed from a composite tubular element attached (e.g. weld, melt, bond, etc.) to the distal portion 15 of the elongate shaft 20.

Because of their intended use in the vasculature, some medical devices are designed to have particular physical characteristics such as flexibility (e.g., for the purposes of this disclosure, flexibility may be also be termed or expressed as bending stiffness or flexural rigidity). For example, some medical devices may be designed to be very stiff in order to provide enough columnar strength to navigate anatomical areas of resistance. Alternatively, some medical devices may be designed flexible enough in order to bend in a manner sufficient to traverse tortuous anatomy. Therefore, at the distal end of the medical device, it may be desirable to tailor the flexibility of the medical device so that the device can effectively reach its target within the vasculature.

In some instances it may be desirable to combine different structural components in order to achieve the desired flexibility and stiffness characteristics of a support catheter. For example, it may be desirable to combine (e.g. weld, melt, bond, etc.) one or more different shaft configurations (e.g. different materials, dimensions, etc.) and/or coil configurations with one another to achieve a desired performance output. However, combining different structural components may require a longer and more complex manufacturing process. Therefore, in some instances it may be desirable to tailor and integrate single-piece components into a finished medical device in order that they exhibit desired performance properties. For example, removing material from a single-piece catheter shaft or coil may provide the same benefit as combining two or more non-tailored components. The tailored component may then be integrated into the overall catheter design.

Figure 3:
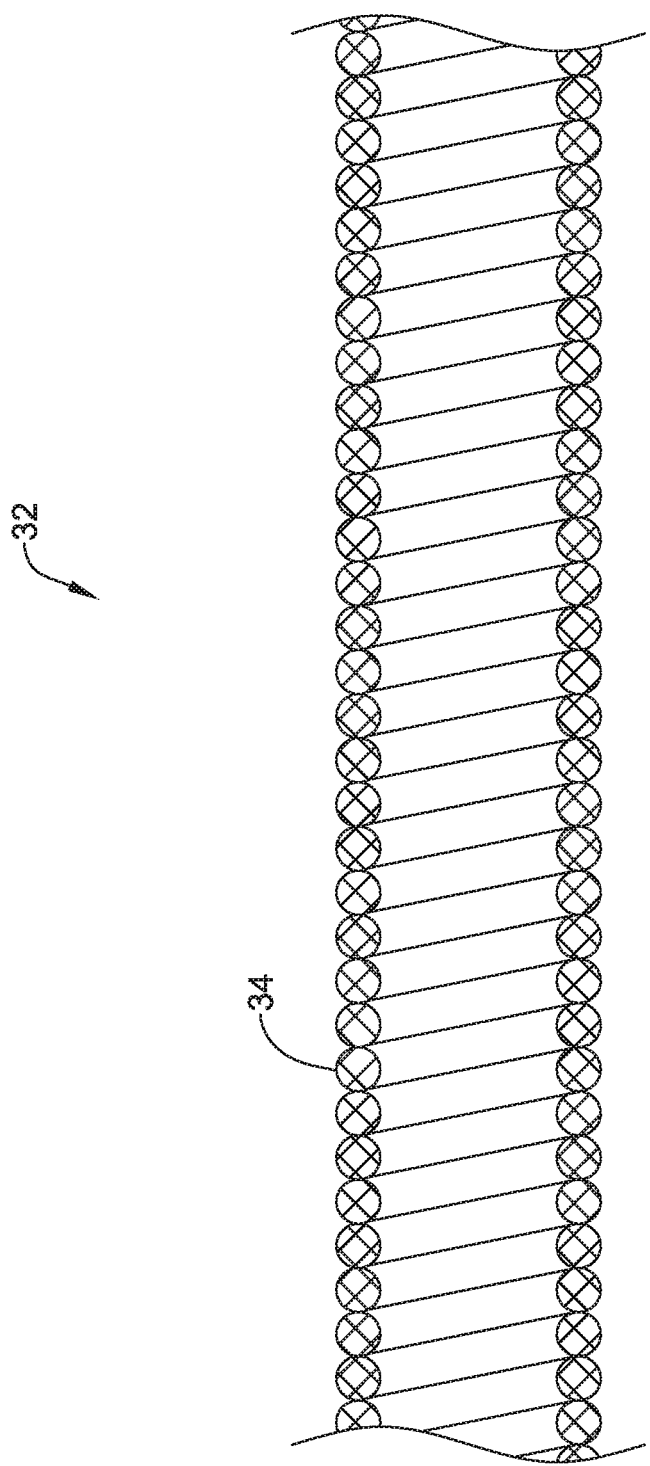
FIG. 3 is a cross-sectional view of an illustrative support member.

FIG. 3 shows an embodiment of a support member 32 that may be utilized in or with the support catheter 10 and/or other devices disclosed herein. In this embodiment, the support member 32 may take the form of a coil. However, in other embodiments, support member 32 may take the form of a braid or other support member. The support member or coil 32 may include one or more filars 34. For purposes of this discussion, a "filar" may be understood as a wire or wires that are wound into a coiled configuration in order to form or otherwise define coil 32. As can be seen in FIG. 3, the filar 34 may have a uniform cross-sectional diameter and pitch. While a uniform cross-sectional diameter is shown in FIG. 3, it is contemplated that the cross-sectional diameter of the filar 34 may vary across the length of the coil 32. Additionally, the coil 32 may be configured to have an open pitch, a closed pitch or combinations thereof. For example, FIG. 3 shows the filar 34 arranged such that there is no space between the individual windings. The absence of space between the windings may be referred to as a "closed" pitch configuration. A closed pitch configuration may be desirable to provide increased column strength to a given component of a medical device. An open pitch configuration may be defined as space existing between adjacent windings of the filar 34. Further, characteristics such as the filar cross-sectional dimension and/or shape, material, orientation and spacing may contribute to the overall configuration and performance (e.g. flexibility, pushability, trackability, column stiffness, etc.) of the coil 32.

Figure 4:
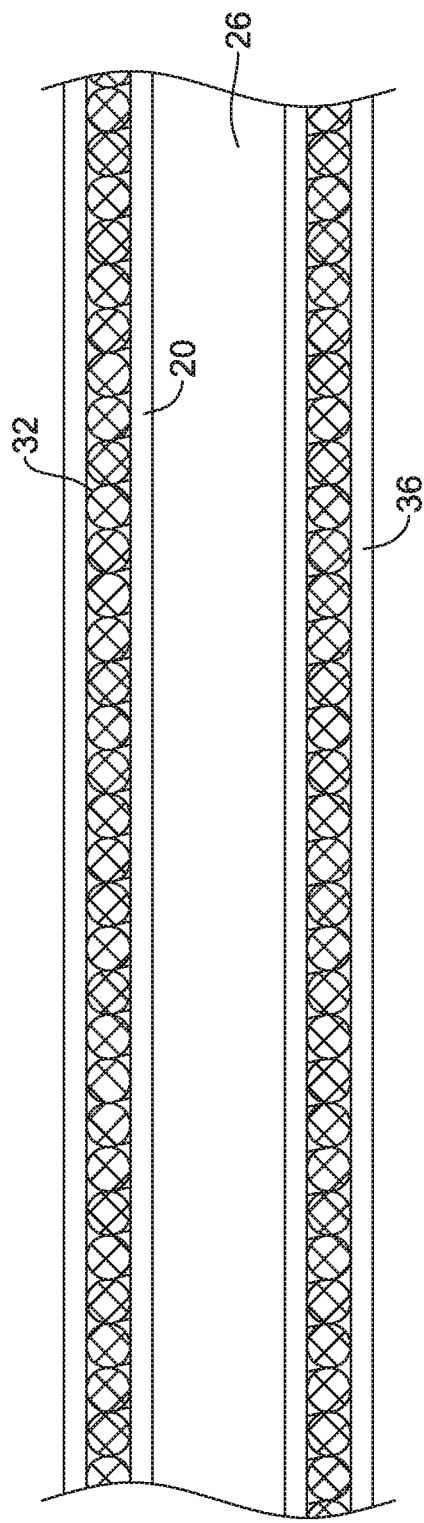
FIG. 4 is a cross-sectional view of a support member disposed over an elongate shaft.

As stated above, in some instances in may be desirable to perform a manufacturing process to tailor the design configuration of a medical device component. Examples of such manufacturing processes and design configurations are described in commonly assigned U.S. Patent Application Ser. No. 62/040,251, the entire disclosure of which is hereby incorporated by reference. Additionally, or alternatively, it may be desirable to further tailor the performance characteristics of catheter 10 by adding additional materials and/or layers onto existing components. For example, the support catheter 10 may incorporate a support member, such as support member 32, into at least a portion of the elongate shaft. FIG. 4 illustrates an embodiment in which a support member 32 has been disposed over a portion of the elongate shaft 20. Additionally, or alternatively, an outer layer 36 may be disposed over the support member 32. In some instances, the outer layer 36 may sit atop the support member 32. In other instances, however, the outer layer 36 may squeeze down and/or pinch the support member 32 onto the shaft 20. While not explicitly shown, the support member 32 may be embedded in the elongate shaft 20 and/or the outer layer 36.

Additionally, the outer layer 36 may be formed of one or more polymer and/or plastic materials along a length or thickness thereof. For example, the outer layer 36 may include two materials having different material properties (e.g. durometer, tensile strength, etc.). It is also understood that the outer layer 36 may include materials other than polymers or plastics. For example, the outer layer 36 may include polymers, metals, ceramics, composites materials, combinations thereof, and the like.

It is contemplated that the support member 32 may be incorporated into any portion of the elongate shaft 20 desired. For example, the support member 32 may be incorporated into the proximal portion 13, the intermediate portion 17, the distal portion 15, or combinations thereof. In some instances, the support member 32 may not be incorporated into any portion of the elongate shaft 20. It is contemplated that the proximal portion 13 and the intermediate portion 17 may include a variety of configurations. In some embodiments, the proximal and/or intermediate portions 13, 17 may include a hypotube. In other embodiments, the proximal and/or intermediate portions 13, 17 may include a polymer shaft and/or a composite material. It is further contemplated that the proximal and/or intermediate portions 13, 17 may be formed from a coiled structure, similar to the support member 32. The filars 34 forming the support member 32 may have varying cross-sectional shapes. For example, the filars 34 may take the form of wires having a generally circular cross-sectional shape. Alternatively, the filars 34 may take the form of ribbons having a generally rectangular shape. Other potential cross-sectional shapes may include, but are not limited to: square, oblong, triangular, polygonal, etc.

Figure 10:
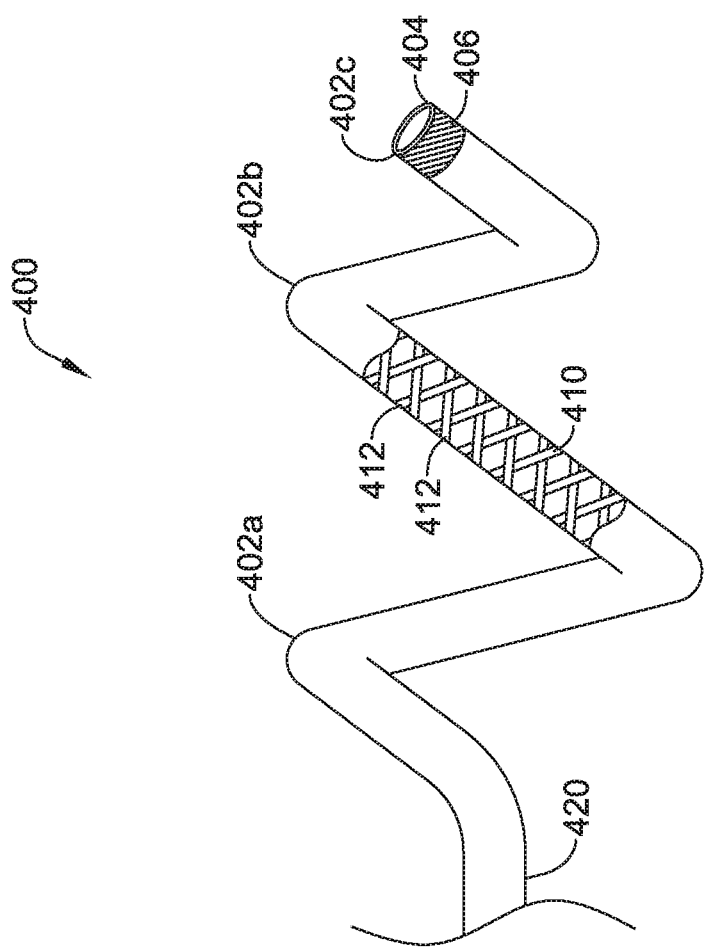
FIG. 10 is a side view of a distal end of another illustrative medical device.

The proximal and/or intermediate portions 13, 17 may also be formed from or otherwise include a braided shaft, similar to the braided element 410 described with respect to FIG. 10. It is contemplated that the braid may be formed from a single filament or a plurality of filaments, as desired. In some instances, a plurality of filaments may be wound together to be used as a single filaments. The filaments may take the form of wires having a generally circular cross-sectional shape. Alternatively, the filaments may take the form of ribbons having a generally rectangular shape. Other potential cross-sectional shapes may include, but are not limited to: square, oblong, triangular, polygonal, etc. The filaments may be made of any material desired, such as, but not limited, metals, metal alloys, polymers, etc.

Figure 9:
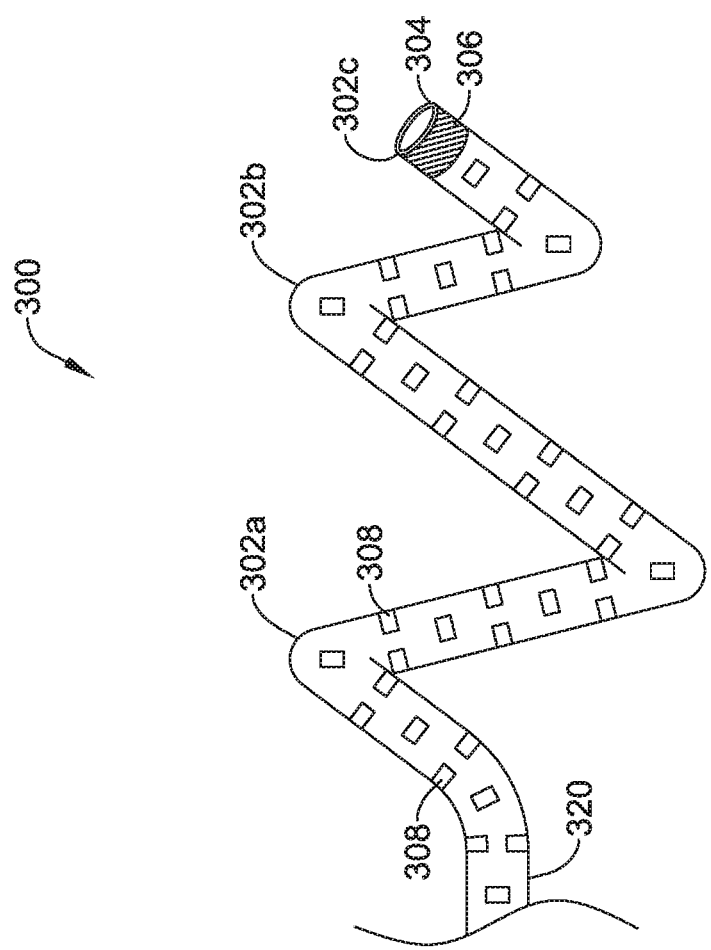
FIG. 9 is a side view of a distal end of another illustrative medical device.

In yet other embodiments, the proximal and/or intermediate portions 13, 17 may be formed from or take the form of a slotted tube, similar to the slots 308 described with respect to FIG. 9. The slotted tube may include a plurality of grooves, slits, slots, holes, openings, or the like, formed in a portion of, or along the entire length thereof. In some embodiments, the slots may completely penetrate the body wall of the slotted tube. In other cases, only some of the slots completely penetrate the body wall. In such cases, some or all of the slots may only partially extend into the body wall of the slotted tube, either on the interior or exterior surface thereof. The shape and size of the slots can vary to achieve the desired characteristics. For example, the shape of the slots can vary to include essentially any appropriate shape, such as, but not limited to square, triangular, round, rectangular, pill-shaped, oval, polygonal, diamond, elongate, irregular, spiral (which may or may not vary in pitch), or other suitable means or the like, and may include rounded or squared edges, and can be variable in length and width, total open area, and the like. In some instances, the slots may have a generally rectangular shape with the major length of the rectangle extending generally parallel to a longitudinal axis of the elongate shaft 20. In other instances, the slots may have a major length that extends generally perpendicular to the longitudinal axis of the elongate shaft 20 or at an oblique angle to the longitudinal axis of the elongate shaft 20.

It is further contemplated that the proximal and/or intermediate portions 13, 17 may include a combination of any of the above structures. For example, the structures described above may be combined to achieve an elongate shaft 20 having the desired flexibility profile. It is further contemplated that the characteristics of a single structure type (for example, but not limited to, the slots in a slotted tube) may be varied along the length of the elongate shaft 20 to achieve the desired characteristics. Further, while the above structures were described relative to the proximal and/or intermediate portion of the elongate shaft 20, it is contemplate that the structures described above may be incorporated into portions of the distal portion 15, as desired.

In some embodiments, the elongate shaft 20 may transition from a stiffer, more rigid (or less flexible) configuration to a more flexible (or less rigid) configuration in a step-wise, or abrupt, manner or a gradual tapered transition, as desired. It is contemplated that there may be a single transition zone (step-wise or tapered) between a stiffer portion to a more flexible portions. In other embodiments, there may be two or more transition zones which define three or more regions having differing flexibility characteristics. For example, a first proximal region may have a first flexibility, a second intermediate region, distal to the first proximal region, may have a second flexibility greater than the first flexibility, and a third distal region, distal to the intermediate region, may have a third flexibility greater than both the first and second flexibilities. In other embodiments, the elongate shaft 20 may include three, four, or more transition zones. It is further contemplated that the elongate shaft 20 may have a flexibility that continuously changes from the proximal portion 13, through the intermediate portion 17, and sometimes into the distal portion 15. In some instances, the elongate shaft 20 may have a flexibility profile in which the regions of more flexibility are alternated with regions of less flexibility. For example, the flexibility of the elongate shaft 20 does not necessarily have to become progressively more flexible towards the distal end 22.

Figure 5:
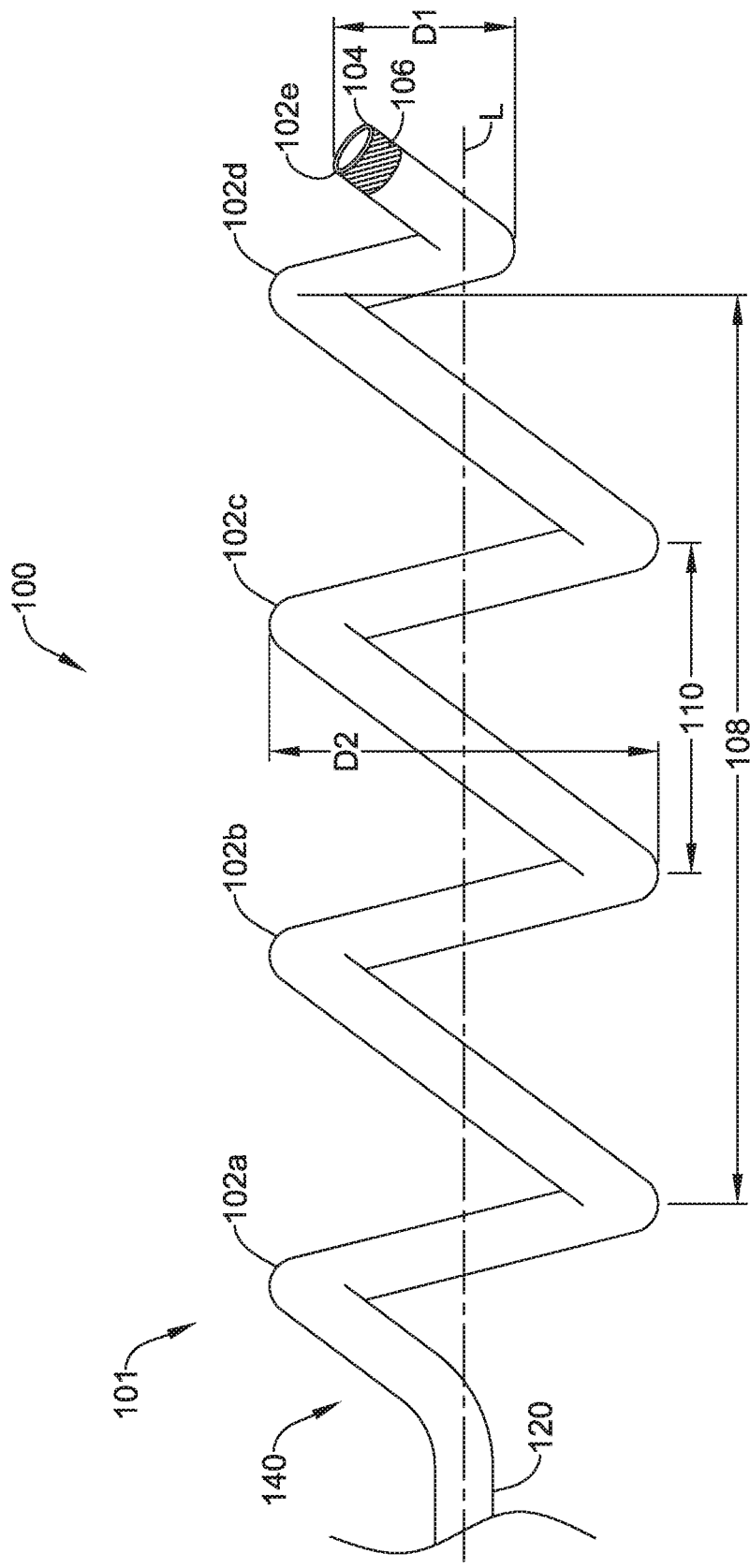
FIG. 5 is a side view of a distal end of an illustrative medical device.
Figure 5A:
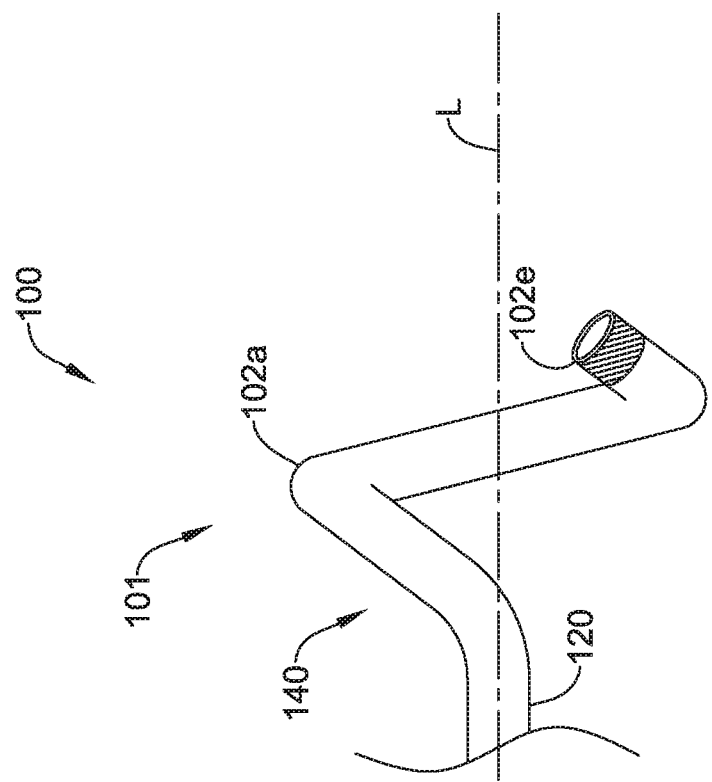
FIG. 5A is a side view of a distal end view of another illustrative medical device.

FIG. 5 is a side view of a distal section 100 of an illustrative support catheter 101. The distal section 100 may be similar in form and function to the distal section 14 described above. The distal section 100 may extend distally from an elongate shaft 120. The elongate shaft 120 may be similar in form and function to the elongate shaft 20 described above. The distal section 100 may generally take the form of a helix having a plurality of windings or connected rings 102a, 102b, 102c, 102d, 102e (collectively 102). While the distal section 100 is illustrated as including approximately five rings 102, it is contemplated that the distal section 100 may include any number of rings desired, such as, but not limited to, one, two, three, four, or more. The distal section 100 may include a proximal ring 102a, a distal ring 102e, and a plurality of rings 102b, 102c, 102d disposed therebetween. In some embodiments, the proximal ring 102a and the distal ring 102e may not form a complete (e.g. 360°) winding, although this is not required, as shown in FIG. 5A. For example, the proximal ring 102a and the distal ring 102e may individually or together form a winding that is less than 360°, e.g. the entire helix may be less than 360°. An intermediate region 108 of the distal section 100 may include all of the rings 102b, 102c, 102d except for the most proximal ring 102a and the most distal ring 102e. The intermediate region 108 may include any number of rings desired, such as, but not limited to, zero, one two, three, four, or more. In some embodiments, the distal section 100 may include one or more radiopaque markers 106. A radiopaque marker 106 may be positioned adjacent to the distal end 104 of the distal section 100. Additionally or alternatively, one or more radiopaque markers may be positioned at any point along the length of the distal section 100 and/or the elongate shaft 120 as desired.

The catheter 101 may transition from the generally straight elongate shaft 120 to the helically wound distal section 100 at a transition zone or entry point 140 positioned adjacent to the proximal ring 102a. It is contemplated that the entry point 140 may be along a longitudinal axis L of the elongate shaft 120 and/or a center line of the coiled distal section 100. In other embodiments, the entry point 140 may be at the outer diameter of the proximal ring 102a or at point between the center line L and the outer diameter of the proximal ring 102a. In yet other embodiments, the entry point 140 may be a point outside of the coiled distal section 100. The entry point 140 may have a radius of curvature that is the same or different from the radius of curvature of the proximal ring 102a. In some embodiments, a radius of curvature of the entry point 140 may be less than a radius of curvature of the proximal ring 102a. In other embodiments, a radius of curvature of the entry point 140 may be greater than a radius of curvature of the proximal ring 102a.

Figure 6:
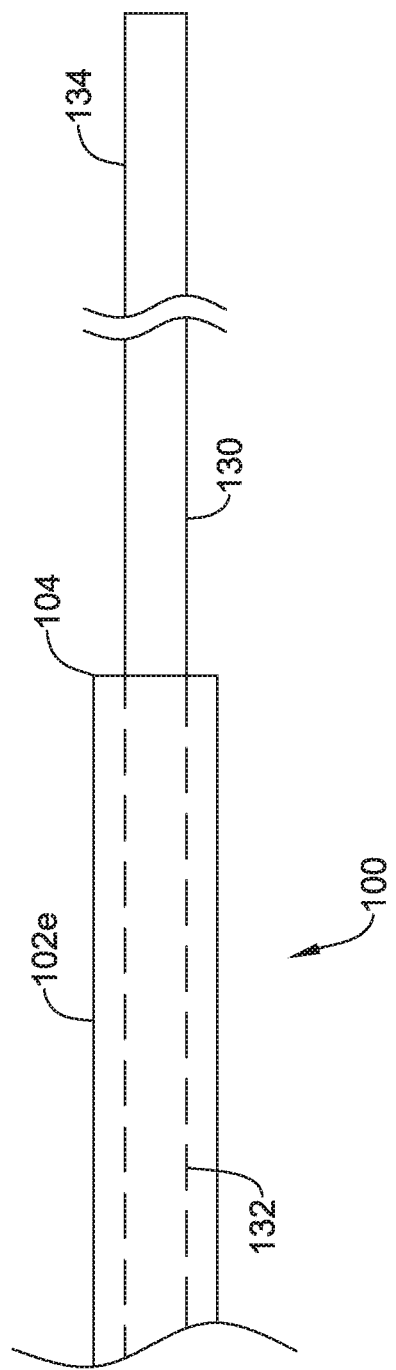
FIG. 6 is a side view of the distal end of the illustrative medical device of FIG. 5 disposed over a proximal portion of another illustrative medical device.
Figure 7:
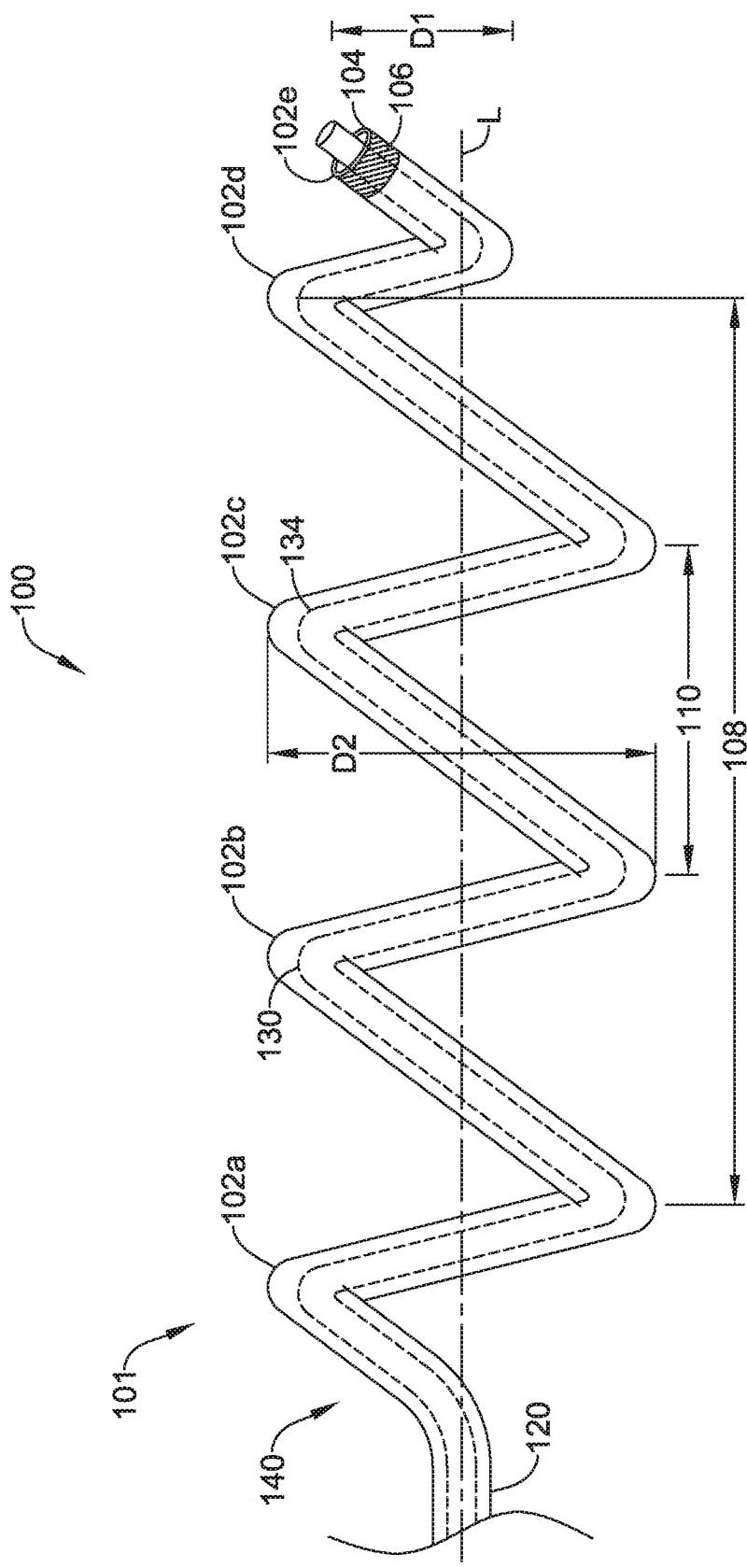
FIG. 7 is a side view of the distal end of the illustrative medical device of FIG. 5 disposed over a distal portion of another illustrative medical device.

Referring briefly to FIGS. 6 and 7, which illustrate the support catheter 101 of FIG. 5 over a guidewire 130, the helical shape of the distal section 100 may allow the user non-axial bias torqueing of the support member 101 as they target side branch and accessory vessel guidewire access. The distal section 100 may be formed from a polymeric material having a stiffness that is greater than a stiffness of a distal end region 134 of a guidewire 130. For example, a guidewire 130 can be tracked into position and a support catheter 101 may be tracked over the guidewire. As the distal section 100 of the support catheter 101 is tracked over the proximal, stiffer portion 132 of the guidewire, the distal section 100 of the support catheter 101 is straightened to allow for easier advancement of the support catheter 101, as shown in FIG. 6. As the distal section 100 is tracked over the more flexible distal end region 134 of the guidewire, the distal section 100 overcomes the bias of the guidewire 130 and resumes its generally helical shape, as shown in FIG. 7. The distal section 100 can then be used to access the target side branch or accessory vessel. The helical shape of the distal section 100 may help keep the elongate shaft 120 centered in the vessel while also preventing the distal end 104 from dragging on the vessel wall. Once vessel access is gained the guide wire can be advanced. As stiffer wire segments 132 of the guidewire 130 pass through the lumen of the support catheter 101, the distal section 100 may straighten out and allow typical guidewire advancement. Once vessel access is ensured the support catheter may be removed and/or exchanged for more traditional interventional products.

Referring again to FIG. 5, in some embodiments, the distal section 100 may comprise a polymeric tubular element attached (e.g. weld, melt, bond, etc.) to a distal portion of the elongate shaft 120. The distal section 100 may be attached to the elongate shaft 120 such that a lumen of the distal section is in fluid communication with a lumen of the elongate shaft 120. While the distal section 100 is described as attached to the elongate shaft 120, it is contemplated that the distal section 100 may be formed as a unitary or monolithic structure with the elongate shaft 120. The polymeric material may be selected such that the distal section 100 is substantially flexible to straighten while being advanced over a proximal region of the guidewire, yet rigid enough to overcome the bias of a distal region of the guidewire. It is contemplated that the distal section 100 may have a stiffness less than a proximal region of a guidewire but greater than a distal region of the guidewire. In some embodiments, the entire length of the distal section 100 may be formed from a polymeric material, although this is not required.

As discussed above, it is contemplated that portions of the elongate shaft 120 proximal to the distal section 100 may incorporate support members, such as support member 32 or other structural features, such as, but not limited to, coils, braids, slots, and/or hypotubes. The structural features may be configured, selected, and/or positioned to enhance the flexibility, pushability, trackability, column stiffness, etc. of the elongate shaft 120. In some instances, the structural features may extend into the distal section 100, although this is not required. For example, the distal section 100 may transition to a polymer tube (e.g. no additional support structures) element at a location distal to the most proximal ring 102a. The distal section 100 may transition to a polymer tube only element at approximately 4 millimeters (mm) or less, at 3 mm or less, or 2 mm or less from the distal end 104. Alternatively, the distal section 100 may transition to a polymer tube only element at any one of the rings 102. For example, the distal section 100 may transition to a polymer tube only element at the most proximal ring 102a, one of the intermediate rings 102b, 102c, 102d, or at the most distal ring 102e.

In some embodiments, the size, or diameter, of the rings 102 may vary along the length of the distal section 100 between a minimum diameter D1 to a maximum diameter D2. It is contemplated that the minimum diameter D1 may be larger than an outer diameter of the elongate shaft 120. The most proximal ring 102a may have a diameter that is less than a diameter of the next distal ring 102b, although this is not required. While not explicitly shown, the proximal ring 102a may have a diameter that is the same as, substantially the same as, or larger than the diameter of the next distal ring 102b. The most distal ring 102e may have a diameter that is less than the next proximal ring 102d, although this is not required. While not explicitly shown, the distal ring 102e may have a diameter that is the same as, substantially the same as, or larger than the diameter of the next proximal ring 102d. The rings 102b, 102c, 102d disposed within the intermediate region 108 may all have the same diameter. Alternatively, the rings 102b, 102c, 102d disposed within the intermediate region 108 may have differing or varying diameters from one another.

The minimum diameter D1 and/or the maximum diameter D2 of the distal section 100 may be selected based on the diameter of the vessel to be accessed. In some embodiments, the maximum diameter D2 may be approximately the same as the inner diameter of the smallest vessel to be accessed. In other embodiments, the maximum diameter D2 may be less than the inner diameter of the smallest vessel to be accessed. For example, the maximum diameter D2 may be in the range of 90% or less of the inner diameter of the smallest vessel to be accessed, 75% or less, 50% or less, 25% or less, or 10% or less. It is contemplated that in some instances, the maximum diameter D2 may be larger than or slightly larger than the inner diameter of the smallest vessel to be accessed. For example, the maximum diameter D2 may be in the range of 110% of the inner diameter of the smallest vessel to be accessed. In some embodiments, the minimum diameter D1 may be approximately the same as the inner diameter of the smallest vessel to be accessed. In other embodiments, the minimum diameter D1 may be less than the inner diameter of the smallest vessel to be accessed. For example, the minimum diameter D1 may be in the range of 90% or less of the inner diameter of the smallest vessel to be accessed, 75% or less, 50% or less, 25% or less, or 10% or less. It is contemplated that in some instances, the minimum diameter D1 may be larger than or slightly larger than the inner diameter of the smallest vessel to be accessed. In some embodiments, the minimum diameter D1 and the maximum diameter D2 may be the same or approximately the same. In some instances, the minimum diameter D1 may be determined by the size if the guidewire to be used. For example, the minimum diameter D1 may be approximately three to seven times the diameter of the guidewire.

The pitch 110, or the distance between one complete winding or ring, may vary between adjacent rings 102. For example, the proximal ring 102a and the next distal ring 102b may have a first pitch. Ring 102b and ring 102c may have a second pitch, different from the first pitch. The distal ring 102e and the next proximal ring 102d may have a third pitch different from one or both of the first and second pitches. In some embodiments, the first pitch may be less than a pitch, such as the second pitch, of the rings 102b, 102c, 102d in the intermediate section 108. In other embodiments, the first pitch may be greater than a pitch, such as the second pitch, of the rings 102b, 102c, 102d in the intermediate section 108. Similarly, the third pitch may be may be less than or greater than, a pitch, such as the second pitch, of the rings 102b, 102c, 102d in the intermediate section 108. It is further contemplated that the rings 102b, 102c, 102d in the intermediate section 108 may have the same pitch (e.g. same distance between each adjacent ring in the intermediate section 108) or may have differing pitches, as desired. The distal section 100 may be formed such that the pitch continuously increases or decreases along the length of the distal section 100.

Figure 8:
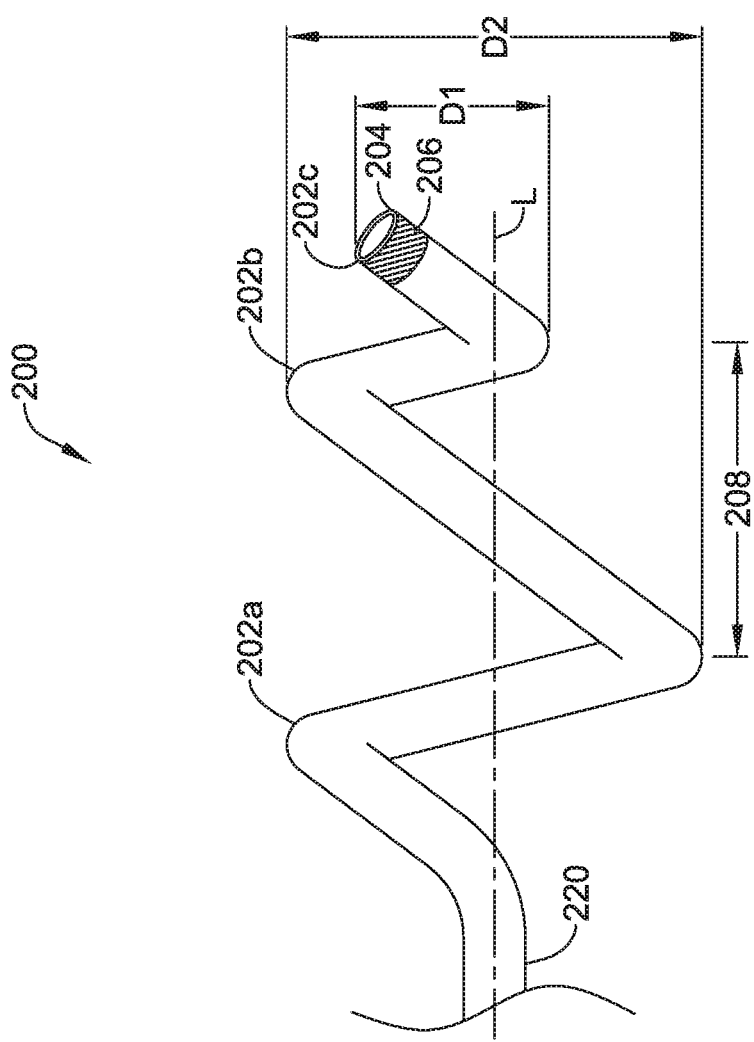
FIG. 8 is a side view of a distal end of another illustrative medical device.

FIG. 8 is a side view of a distal section 200 of another illustrative support catheter. The distal section 200 may be similar in form and function to the distal sections 14, 100 described above. The distal section 200 may extend distally from an elongate shaft 220. The elongate shaft 220 may be similar in form and function to the elongate shafts 20, 120 described above. The distal section 200 may generally take the form of a helix having a plurality of windings or connected rings 202a, 202b, 202c (collectively 202). While the distal section 200 is illustrated as including approximately three rings 202, it is contemplated that the distal section 200 may include any number of rings desired, such as, but not limited to, one, two, three, four, or more. The distal section 200 may include a proximal ring 202a, a distal ring 202c, and an intermediate ring 202b disposed therebetween. In some embodiments, the proximal ring 202a and the distal ring 202c may not form a complete (e.g. 360°) winding. An intermediate region 208 of the distal section 200 may include any ring(s) 202b except for the most proximal ring 202a and the most distal ring 202c. The intermediate region 208 may include any number of rings desired, such as, but not limited to, one, two, three, four, or more. In some embodiments, the distal section 200 may include one or more radiopaque markers 206. In some instances, a radiopaque marker 206 may be positioned adjacent to the distal end 204 of the distal section 200. In other instances, one or more radiopaque markers may be positioned at any point along the length of the distal section 200 and/or the elongate shaft 220.

In some embodiments, the size, or diameter, of the rings 202 may vary along the length of the distal section 200 between a minimum diameter D1 to a maximum diameter D2. The most proximal ring 202a may have a diameter that is less than a diameter of the intermediate ring 202b, although this is not required. While not explicitly shown, the proximal ring 202a may have a diameter that is the same as, substantially the same as, or larger than the diameter of the intermediate ring 202b. The distal ring 202c may have a diameter that is less than the intermediate ring 202b, although this is not required. While not explicitly shown, the distal ring 202c may have a diameter that is the same as, substantially the same as, or larger than the diameter of intermediate proximal ring 202b.

The minimum diameter D1 and/or the maximum diameter D2 of the distal section 200 may be selected based on the diameter of the vessel to be accessed. In some embodiments, the maximum diameter D2 may be approximately the same as the inner diameter of the smallest vessel to be accessed. In other embodiments, the maximum diameter D2 may be less than the inner diameter of the smallest vessel to be accessed. For example, the maximum diameter D2 may be in the range of 90% or less of the inner diameter of the smallest vessel to be accessed, 75% or less, 50% or less, 25% or less, or 10% or less. It is contemplated that in some instances, the maximum diameter D2 may be larger than or slightly larger than the inner diameter of the smallest vessel to be accessed. For example, the maximum diameter D2 may be in the range of 110% of the inner diameter of the smallest vessel to be accessed. In some embodiments, the minimum diameter D1 may be approximately the same as the inner diameter of the smallest vessel to be accessed. In other embodiments, the minimum diameter D1 may be less than the inner diameter of the smallest vessel to be accessed. For example, the minimum diameter D1 may be in the range of 90% or less of the inner diameter of the smallest vessel to be accessed, 75% or less, 50% or less, 25% or less, or 10% or less. It is contemplated that in some instances, the minimum diameter D1 may be larger than or slightly larger than the inner diameter of the smallest vessel to be accessed. In some embodiments, the minimum diameter D1 and the maximum diameter D2 may be the same or approximately the same. In some instances, the minimum diameter D1 may be determined by the size if the guidewire to be used. For example, the minimum diameter D1 may be approximately three to seven times the diameter of the guidewire.

The pitch, or the distance between one complete winding or ring, may vary between adjacent rings 202. For example, the proximal ring 202a and intermediate ring 202b may have a first pitch. The distal ring 202c and the intermediate ring 202b may have a second pitch. In some embodiments, the first pitch may be the same as the second pitch. In other embodiments, the first pitch may be different than the second pitch.

FIG. 9 is a side view of a distal section 300 of another illustrative support catheter. The distal section 300 may be similar in form and function to the distal sections 14, 100, 200 described above. The distal section 300 may extend distally from an elongate shaft 320. The elongate shaft 320 may be similar in form and function to the elongate shafts 20, 120, 220 described above. The distal section 300 may generally take the form of a helix having a plurality of windings or connected rings 302a, 302b, 302c (collectively 302). While the distal section 300 is illustrated as including approximately three rings 302, it is contemplated that the distal section 300 may include any number of rings desired, such as, but not limited to, one, two, three, four, or more. The distal section 300 may include a proximal ring 302a, a distal ring 302c, and an intermediate ring 302b disposed therebetween. In some embodiments, the proximal ring 302a and the distal ring 302c may not form a complete (e.g. 360°) winding. In some embodiments, the distal section 300 may include one or more radiopaque markers 306. In some instances, a radiopaque marker 306 may be positioned adjacent to the distal end 304 of the distal section 300. In other instances, one or more radiopaque markers may be positioned at any point along the length of the distal section 300 and/or the elongate shaft 320.

It is contemplated that portions of the elongate shaft 320 proximal to the distal section 300 may incorporate support members, such as support member 32 or other structural features, such as, but not limited to, coils, braids, slots, and/or hypotubes. The structural features may be configured, selected, and/or positioned to enhance the flexibility, pushability, trackability, column stiffness, etc. of the elongate shaft 320. The distal section 300 may also include structure features configured, selected, and/or positioned to enhance the flexibility, pushability, trackability, column stiffness, etc. of the distal section 300. It is contemplated that the distal section 300 may include the same structural features as the elongate shaft 320, or different structural features, as desired. In some embodiments, the elongate shaft 320 and/or distal section 300 may include a combination of structural features to achieve the desired properties. For example, a first portion of the distal section 300 may include a first structural feature and a second portion of the distal section 300 may include a second, different, structural feature in addition to or in place of the first structural feature. It is contemplated that the distal section 300 may include any number of or combinations of structural features desired to achieve the desired properties.

In some embodiments, the distal section 300 may comprise a plurality of slots 308. The slots 308 may include a plurality of grooves, slits, slots, holes, openings, or the like, formed in a portion of, or along the entire length thereof. While not explicitly shown, the slots 308 may also be formed in the elongate shaft 320. However, the distal section 300 does not necessarily include the same structural features as portions of the elongate shaft 320. In some embodiments, the slots 308 may completely penetrate the body wall of the distal section 300. In other cases, only some of the slots 308 completely penetrate the body wall. In such cases, some or all of the slots 308 may only partially extend into the body wall of the distal section 300, either on the interior or exterior surface thereof. The shape and size of the slots 308 can vary to achieve the desired characteristics. For example, the shape of the slots 308 can vary to include essentially any appropriate shape, such as, but not limited to square, triangular, round, rectangular, pill-shaped, oval, polygonal, diamond, elongate, irregular, spiral (which may or may not vary in pitch), or other suitable means or the like, and may include rounded or squared edges, and can be variable in length and width, total open area, and the like. In some instances, the slots 308 may have a generally rectangular shape with the major length of the rectangle extending generally parallel to a longitudinal axis of the elongate shaft 320, when the distal section 300 is in a generally straight configuration. In other instances, the slots 308 may have a major length that extends generally perpendicular to the longitudinal axis of the elongate shaft 320 or at an oblique angle to the longitudinal axis of the elongate shaft, when the distal section 300 is in a generally straight configuration. The slots 308 may extend over the entire length of the distal section 300 or over only a portion of the length thereof.

FIG. 10 is a side view of a distal section 400 of another illustrative support catheter. The distal section 400 may be similar in form and function to the distal sections 14, 100, 200, 300 described above. The distal section 400 may extend distally from an elongate shaft 420. The elongate shaft 420 may be similar in form and function to the elongate shafts 20, 120, 220, 320 described above. The distal section 400 may generally take the form of a helix having a plurality of windings or connected rings 402a, 402b, 402c (collectively 402). While the distal section 400 is illustrated as including approximately three rings 402, it is contemplated that the distal section 400 may include any number of rings desired, such as, but not limited to, one, two, three, four, or more. The distal section 400 may include a proximal ring 402a, a distal ring 402c, and an intermediate ring 402b disposed therebetween. In some embodiments, the proximal ring 402a and the distal ring 402c may not form a complete (e.g. 360°) winding. In some embodiments, the distal section 400 may include one or more radiopaque markers 406. In some instances, a radiopaque marker 406 may be positioned adjacent to the distal end 404 of the distal section 400. In other instances, one or more radiopaque markers may be positioned at any point along the length of the distal section 400 and/or the elongate shaft 420.

It is contemplated that portions of the elongate shaft 420 proximal to the distal section 400 may incorporate support members, such as support member 32 or other structural features, such as, but not limited to, coils, braids, slots, and/or hypotubes. The structural features may be configured, selected, and/or positioned to enhance the flexibility, pushability, trackability, column stiffness, etc. of the elongate shaft 420. The distal section 400 may also include structure features configured, selected, and/or positioned to enhance Hi the flexibility, pushability, trackability, column stiffness, etc. of the distal section 400. It is contemplated that the distal section 400 may include the same structural features as the elongate shaft 420, or different structural features, as desired. In some embodiments, the elongate shaft 420 and/or distal section 400 may include a combination of structural features to achieve the desired properties. For example, a first portion of the distal section 400 may include a first structural feature and a second portion of the distal section 400 may include a second, different, structural feature in addition to or in place of the first structural feature. It is contemplated that the distal section 400 may include any number of or combinations of structural features desired to achieve the desired properties.

In some embodiments, the distal section 400 may be formed from, or otherwise include, a braided element 410. While not explicitly shown, the braided element 410 may also be incorporated into the elongate shaft 420. However, the distal section 400 does not necessarily include the same structural features as portions of the elongate shaft 420. It is contemplated that the braid 410 may be formed from a single filament or a plurality of filaments 412, as desired. In some instances, a plurality of filaments may be wound together to be used as a single filaments. The filaments 412 may take the form of wires having a generally circular cross-sectional shape. Alternatively, the filaments may take the form of ribbons having a generally rectangular shape. Other potential cross-sectional shapes may include, but are not limited to: square, oblong, triangular, polygonal, etc. The filaments 412 may be made of any material desired, such as, but not limited, metals, metal alloys, polymers, etc.

In some instances, the braided element 410 may be disposed over an inner liner or inner layer. Additionally, or alternatively, an outer layer may be disposed over the braided element 410. In some instances, the outer layer may sit atop the braided element 410. In other instances, however, an outer layer may squeeze down and/or pinch the braided element 410 onto the inner liner. While not explicitly shown, the braided element 410 may be embedded in the distal section 400. It is contemplated that the distal section 400 may be formed entirely of the braided element 410 without an inner layer or outer layer. The braided element 410 may extend over the entire length of the distal section 400 or only a portion of the length thereof.

Figure 11:
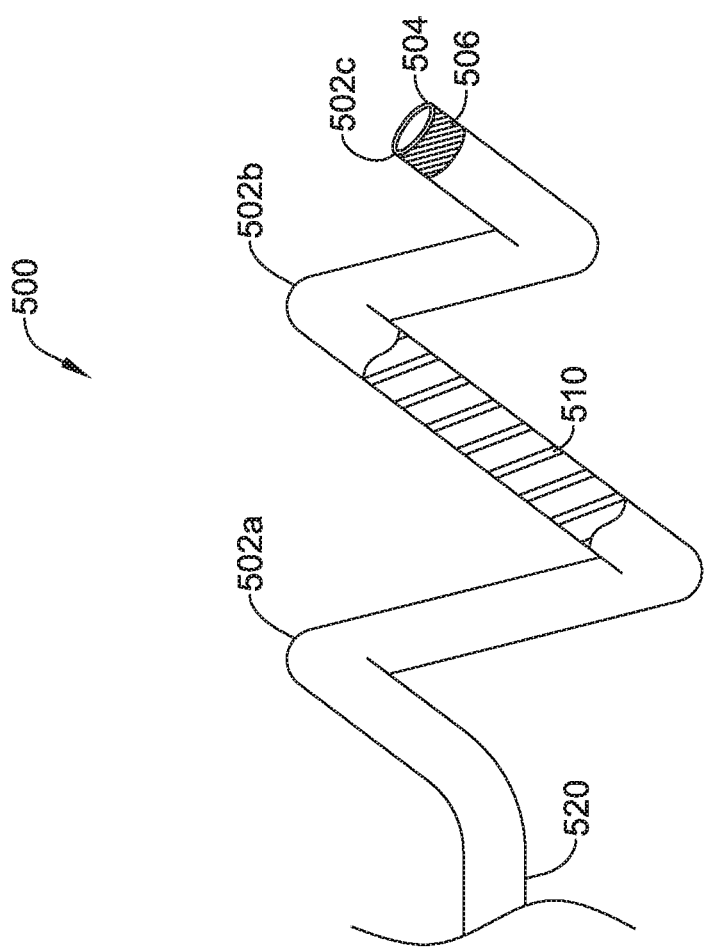
FIG. 11 is a side view of a distal end of another illustrative medical device.

FIG. 11 is a side view of a distal section 500 of another illustrative support catheter. The distal section 500 may be similar in form and function to the distal sections 14, 100, 200, 300, 400 described above. The distal section 500 may extend distally from an elongate shaft 520. The elongate shaft 520 may be similar in form and function to the elongate shafts 20, 120, 220, 320, 420 described above. The distal section 500 may generally take the form of a helix having a plurality of windings or connected rings 502a, 502b, 502c (collectively 502). While the distal section 500 is illustrated as including approximately three rings 502, it is contemplated that the distal section 500 may include any number of rings desired, such as, but not limited to, one, two, three, four, or more. The distal section 500 may include a proximal ring 502a, a distal ring 502c, and an intermediate ring 502b disposed therebetween. In some embodiments, the proximal ring 502a and the distal ring 502c may not form a complete (e.g. 360°) winding. In some embodiments, the distal section 500 may include one or more radiopaque markers 506. In some instances, a radiopaque marker 506 may be positioned adjacent to the distal end 504 of the distal section 500. In other instances, one or more radiopaque markers may be positioned at any point along the length of the distal section 500 and/or the elongate shaft 520.

It is contemplated that portions of the elongate shaft 520 proximal to the distal section 500 may incorporate support members, such as support member 32 or other structural features, such as, but not limited to, coils, braids, slots, and/or hypotubes. The structural features may be configured, selected, and/or positioned to enhance the flexibility, pushability, trackability, column stiffness, etc. of the elongate shaft 520. The distal section 500 may also include structure features configured, selected, and/or positioned to enhance the flexibility, pushability, trackability, column stiffness, etc. of the distal section 500. It is contemplated that the distal section 500 may include the same structural features as the elongate shaft 520, or different structural features, as desired. In some embodiments, the elongate shaft 520 and/or distal section 500 may include a combination of structural features to achieve the desired properties. For example, a first portion of the distal section 500 may include a first structural feature and a second portion of the distal section 500 may include a second, different, structural feature in addition to or in place of the first structural feature. It is contemplated that the distal section 500 may include any number of or combinations of structural features desired to achieve the desired properties.

In some embodiments, the distal section 500 may be formed from, or otherwise include, a coiled element 510. While not explicitly shown, the coiled element 510 may also be incorporated into the elongate shaft 520. However, the distal section 500 does not necessarily include the same structural features as portions of the elongate shaft 520. It is contemplated that the coil 510 may be formed from a single filament or a plurality of filaments, as desired, that are wound into a coiled configuration. The coil 510 may be similar in form and function to the support member 32 described above. The coil 510 may be configured to have an open pitch, a closed pitch or combinations thereof. Further, characteristics such as the filar cross-sectional dimension and/or shape, material, orientation and spacing may contribute to the overall configuration and performance (e.g. flexibility, pushability, trackability, column stiffness, etc.) of the coil 510.

In some instances, the coiled element 510 may be disposed over an inner liner or inner layer. Additionally, or alternatively, an outer layer may be disposed over the coiled element 510. In some instances, the outer layer may sit atop the coiled element 510. In other instances, however, an outer layer may squeeze down and/or pinch the coiled element 510 onto the inner liner. While not explicitly shown, the coiled element 510 may be embedded in the distal section 500. It is contemplated that the distal section 500 may be formed entirely of the coiled element 510 without an inner layer or outer layer. The coiled element 510 may extend over the entire length of the distal section 500 or only a portion of the length thereof.

The materials that can be used for the various components of the support catheter 10 (and/or other medical devices disclosed herein) and the various tubular members disclosed herein may include those commonly associated with medical devices. For simplicity purposes, the following discussion makes reference to the support catheter 10. However, this is not intended to limit the devices and methods described herein, as the discussion may be applied to other similar medical devices and/or components of medical devices disclosed herein.

The support catheter 10 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICK- ELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the support catheter 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of Magnetic Resonance Imaging (MM) compatibility is imparted into the support catheter 10. For example, the support catheter 10, or portions thereof, may be made of a material that does not substantially distort the image and create substantial artifacts (i.e., gaps in the image). Certain ferromagnetic materials, for example, may not be suitable because they may create artifacts in an MM image. The support catheter 10, or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical device configured to facilitate placement of a guidewire, comprising:
   an elongate shaft having a proximal region, a distal region, and a lumen extending therebetween;
   a helical section extending distally from the distal region of the elongate shaft, the helical section comprising a tubular member wound into a helix including a plurality of rings; and
   a manifold affixed to the proximal region of the elongate shaft;
   wherein the plurality of rings each have an outer diameter and the outer diameter of a proximal-most ring of the plurality of rings is greater than the outer diameter of a distal-most ring of the plurality of rings; and wherein the smallest of any of the outer diameters of the plurality of rings is greater than an outer diameter of the elongate shaft; and wherein the helical section is configured to be biased into straight when disposed over a proximal portion of a guidewire and bias the guidewire into a helical configuration when disposed over a distal portion of a guidewire so as to direct the guidewire in a direction non-parallel to a longitudinal axis of the elongate shaft.

2. The medical device of claim 1, wherein the helix comprises at least one of the proximal-most ring or the distal-most ring having less than a 360° revolution.

3. The medical device of claim 1, wherein the helix comprises one or more intermediate rings disposed between the proximal-most ring and the distal-most ring.

4. The medical device of claim 2, wherein a pitch of the helical section varies from a proximal end of the helical section to a distal end of the helical section.

5. The medical device of claim 2, wherein the pitch of the helical section is the same from a proximal end of the helical section to a distal end of the helical section.

6. The medical device of claim 1, further comprising a plurality of slots in a wall of the tubular member.

7. The medical device of claim 1, further comprising a braided element extending along a portion of the tubular member.

8. The medical device of claim 1, further comprising a coiled element extending along a portion of the tubular member.

9. A medical device for facilitating placement of a guidewire, comprising:

an elongate shaft having a proximal region, a distal region, and a lumen extending therebetween;

a helical section extending distally from the distal region of the elongate shaft, the helical section comprising a tubular member wound into a helix including a plurality of rings and having a lumen in communication with the lumen of the elongate shaft; and a manifold affixed to the proximal region of the elongate shaft;

wherein the plurality of rings each have an outer diameter and the smallest of any of the outer diameters of the plurality of rings is greater than an outer diameter of the elongate shaft; and wherein the helical section is configured to be biased into straight when disposed over a proximal portion of a guidewire and bias the guidewire into a helical configuration when disposed over a distal portion of a guidewire so as to direct the guidewire in a direction non-parallel to a longitudinal axis of the elongate shaft.

10. The medical device of claim 9, wherein the helix comprises a ring having less than a 360° revolution.

11. The medical device of claim 9, wherein a pitch of the helical section varies from a proximal end of the helical section to a distal end of the helical section.

12. The medical device of claim 9, wherein the outer diameter of the proximal-most ring is greater than the outer diameter of the distal-most ring.

13. The medical device of claim 9, wherein the elongate shaft has a first stiffness and the helical section has a second stiffness less than the first stiffness.

* * * * *